United States Patent [19]

Franx

[11] Patent Number: 4,545,889

[45] Date of Patent: Oct. 8, 1985

[54] GAS ANALYSIS APPARATUS

[75] Inventor: Cornelis Franx, Eindhoven, Netherlands

[73] Assignee: U.S. Philips Corporation, New York, N.Y.

[21] Appl. No.: 678,328

[22] Filed: Dec. 5, 1984

[30] Foreign Application Priority Data

Dec. 6, 1983 [NL] Netherlands .................. 8304182

[51] Int. Cl.⁴ .................................. G01N 27/58
[52] U.S. Cl. .................... 204/406; 204/425; 204/426
[58] Field of Search ............... 204/406, 424, 425, 426, 204/427, 428, 429

[56] References Cited

U.S. PATENT DOCUMENTS

| | | | |
|---|---|---|---|
| 3,514,377 | 5/1970 | Spacil et al. | 204/425 X |
| 3,691,023 | 9/1972 | Ruka et al. | 204/425 X |
| 3,907,657 | 9/1975 | Heijne et al. | 204/406 |
| 4,272,329 | 6/1981 | Hetrick et al. | 204/406 X |
| 4,272,330 | 6/1981 | Hetrick | 204/425 X |
| 4,272,331 | 6/1981 | Hetrick | 204/425 X |
| 4,384,935 | 5/1983 | De Jong | 204/406 |

*Primary Examiner*—Andrew H. Metz
*Assistant Examiner*—Nam X. Nguyen
*Attorney, Agent, or Firm*—Robert T. Mayer; Bernard Franzblau

[57] ABSTRACT

A gas analysis apparatus for measuring the concentration of a gas component in a first space. The apparatus comprises a sealed measurement space, of which at least one wall portion consists of a separation wall which exhibits ionic conduction. The concentration of the gas component in the measurement space is changed periodically between two values by filling and pumping currents at the separation wall. The time intervals are measured and are a measure of the concentration. However, these time intervals comprise a "dead time" caused by switch-on and switch-off (both electrical and physical) transients. When given time intervals are combined by addition and subtraction, the influence of dead times can be considerably reduced.

5 Claims, 3 Drawing Figures

GAS ANALYSIS APPARATUS

The invention relates to a gas analysis apparatus for measuring the concentration of a gas component in a first space comprising a sealed measurement space, of which at least one wall portion consists of a separation wall which exhibits ionic conduction and is in contact at least in part via the outer side with the first space, a control unit which periodically supplies during a pumping time interval a pumping current to the separation wall so that by means of an ion current in the separation wall the gas component is removed from the measurement space, and which supplies during a filling time interval a filling current whose polarity is opposite to that of the pumping current so that the gas component is supplied to the measurement space, and further a detection circuit which is connected to electrode layers on either side of the separation wall, the outer electrode layer of which is in contact with the first space, this detection circuit comprising a first voltage detector which supplies a filling interrupt signal for interrupting the filling current when the electrode voltage across the said electrode layers reaches a first reference value, and a second voltage detector which supplies a pumping interrupt signal for interrupting the pumping current when the electrode voltage reaches a second reference value, the electrical charge provided in the separation wall being a measure of the concentration of the gas component.

Such a gas analysis apparatus is known from U.S. Pat. No. 4,384,935.

During the measurement of the electrical charge provided in the separation wall it is assumed that the separation wall, as to its impedance, acts as an electrical resistance so that this charge is to be measured outside the separation wall as supplied and removed charge or as a product of a current to be measured and a time interval to be measured or with constant currents as time intervals.

However, when the various parameters, such as the temperature, the volume of the sealed measurement space, the chosen measurement currents and the measuring range of the concentration to be measured, have such values that the measured time intervals become comparatively small, it is found that the measurement is strongly influenced by switch-on and switch-off transients. In other words, the separation wall is not a pure resistance. It can be derived from a theoretical consideration that the equivalent circuit diagram of the separation wall comprises besides resistances also capacitances, as a result of which RC time constants and stored capacitor charges are obtained.

The said equivalent circuit diagram can be derived by means of impedance measurements at various frequencies, for example, of from 0.1 Hz to 100 kHz, from which diagrams can be drawn in the complex plane. The foregoing can be found, for example, in the article by A. D. Franklin entitled "Electrode Effects in the Measurement of Ionic Conductivity" in "Journal of the American Ceramic Society", Volume 58, Nr. 11/12, November/December 1975, pages 465–473.

It can be demonstrated by means of a physical model of the separation wall that in substantially all conditions a space charge and an electrical field present between an electrode layer and the associated space charge are produced under both electrode layers of a separation wall in the material thereof.

This space charge and hence also the potential of the electrode layer vary in dependence upon the concentration, or pressure, of the gas component at the respective sides of the separation wall.

The difference between the potentials of both electrode layers of a wall indicates via the law of Nernst the relation between the pressures of the gas component on both sides of the wall.

It will be appreciated that with varying pressures the corresponding potential variations again correspond to charge variations, space charge thus being stored or released. These charges are always supplied or removed, i.e. with a separation wall, which is connected via the electrode layers to a supply source for supplying the filling and pumping currents, by means of these currents or, with a separation wall which serves as a sensor and to which a substantially electroless Nernst voltage measurement takes place, by molecule exchange with the ambient gas, therefore also with the measurement space.

These charges do not contribute to the desired pressure variations by means of molecule transport in the measurement space. They become manifest with constant filling and pumping currents in a dead time which forms part of the measurement time. The linear relation between measurement time and pressure to be measured now comprises in the associated diagram besides the inclination of the line also a term which represents the dead time. These two parameters can be found by carrying out two calibration measurements. For this purpose, two well-known gas samples have therefore to be used, of which one, for example for oxygen with a separation wall of zirconium dioxide, may be the atmospheric air. However, it has been found in practice that due to an ageing phenomenon the dead time varies so that a repeated calibration is necessary, which is annoying and expensive.

The invention has for an object to avoid the aforementioned disadvantages and to provide a gas analysis apparatus which can be calibrated by one calibration.

For this purpose, the gas analysis apparatus is characterized in that the detection circuit further comprises a third, a fourth and a fifth voltage detector, which supply an output signal when the electrode voltage reaches a third, a fourth and a fifth reference value, respectively, all these values lying in the range from the first to the second reference value and twice the fourth value being substantially equal to the sum of the third and the fifth values, while as a measure of the concentration of the gas component a difference charge is measured which is equal to the difference between the charge displaced in a first time interval limited by the instants at which the third and the fourth voltage detectors supply their output signals and the charge displaced in a second time interval limited by the instants at which the fourth and the fifth voltage detectors supply their output signals.

The dead time is then substantially zero so that one calibration is sufficient, which can be carried out in the factory during the adjustment of the apparatus. Recalibrations at the service station are seldom necessary, but can be carried out in a simple manner with a gas calibration sample, in the case of oxygen the atmospheric air.

The invention is based on the idea that the influence of a switch-on or switch-off transient on a measurement can be avoided in that the measurements are carried out when these phenomena or their influences have disappeared or remain unchanged so that by means of a suitable subtraction procedure applied to the measurement results these influences compensate each other. Thus, a charge variation at an apparent capacitance in the separation wall, which provides in a given time interval a voltage variation V, can be compensated for a charge variation in another time interval, which provides the same voltage variation, using the fact that charge variation equals capacitance times voltage variation.

The invention can be used during the pumping time interval or during the filling time interval or during both time intervals, while in advantageous embodiments of the invention the measurements can be simplified by the use of current sources, three voltage detectors and pulse time measurements made on the output signal of one detector.

The invention will be described more fully with reference to the drawing. In the drawing:

FIG. 1 shows very diagrammatically the gas analysis apparatus according to the said United States Patent, to which the invention is applied.

Figure 1:
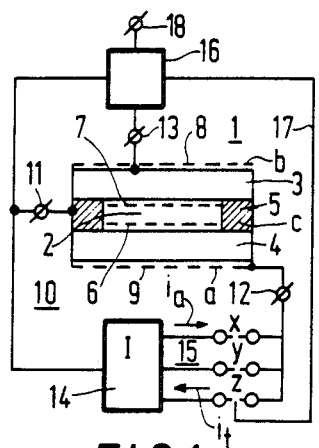
FIG. 1 shows a block circuit diagram of the known apparatus.

A first space 1 encloses, at any rate in part, a sealed measurement space 2, of which a wall portion 3 is a separation wall, which exhibits ionic conduction. The ions are equal to charged atoms or molecules of the gas component to be measured. Another wall portion 4 has the same composition as the wall portion 3. A remaining wall portion 5 is made of metal, for example platinum, porous electrode layers 6 and 7 being connected thereto. On the outer side, the separation walls 3 and 4 are covered with equal electrode layers 8 and 9, respectively. The assembly just described constitutes a measuring device 10 having an electrical connection 11 connected to the wall portion, which has, for example, an annular shape, an electrical connection 12 connected to the layer 9 and an electrical connection 13 connected to the layer 8. A current unit 14 is connected to the connections 11 and 12 and can cause a reversible current to flow through the separation wall 4 by means of a switch 15. The time interval is determined by a detection circuit 16, which controls the switch 15 by a connection 17. In dependence upon the current direction, supply and removal of molecules of the gas component take place both at the layer 6 and at the layer 9. The space 2 will consequently give off gas or will receive gas. In principle, the pressure of the gas component may be larger or smaller than its pressure in the first space 1. However, because of the steeper voltage edges, having the form of a logarithmic function according to Nernst, in a system in which the pressure is lower, this system is used in most cases.

The wall portion 3 is utilized as a sensor by means of which via a voltage measurement at the electrode layers 7 and 8 the desired pressure ratios between the pressure in the first space 1 and the pressure in the measurement space 2 can be determined. For this purpose, the detection circuit 16 is connected to terminals 13 and 11 which are connected to the electrode layers 8 and 7 (via the ring 5). At the connection terminal 18 a pulse train can be derived, the pulse duration of which is the measure of the gas concentration to be measured.

Figure 2:
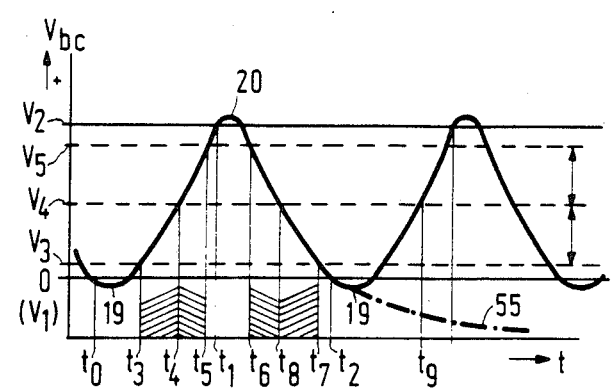
FIG. 2 shows a time diagram of the sensor voltage.

In FIG. 2 the sensor voltage Vbc is plotted against time. The curves shown are mainly parts of the logarithmic function given by Nernst and can be obtained both with the gas analysis apparatus from the known United States Patent and with the apparatus according to the invention. A first voltage detector in the detector circuit of the unit 16 changes over the filling current $i_f$ of the current unit 14 obtained in the position z of the switch 15 at the instant $t_o$ when it detects the first reference value V1, about zero Volts, whereupon the pumping current $i_a$ (in the position x of the switch 15) is switched on. This current is active till the instant $t_1$ at which a second voltage detector supplies a change-over signal when the second reference value V2 is reached. Via the connection 17 the switch 15 is changed over from the position x to the position z, so that now the filling current $i_f$ flows. At the instant $t_2$ the condition as described for $t_o$ is reached again. In the curves an overshoot effect is indicated at 19 and 20, which forms part of the dead time and can be represented by an RC time. FIG. 2 shows that in accordance with the invention this time can be avoided by fixing the measuring time interval at the instants $t_3$ and $t_5$ associated with a third and a fifth reference value V3 and V5, respectively. Similarly, measurements can be obtained at the instants $t_6$ and $t_7$. The dead time is still not entirely eliminated, that is to say that that part is not eliminated which represents, together with the filling or pumping current, a charge variation which corresponds to the product of an effective capacitance in the separation walls and the Nernst voltage variation. For this purpose, in the gas analysis apparatus according to the invention, besides the voltage detectors for the reference values V3 and V5 a fourth voltage detector is provided, which detects the instant at which a reference value V4 is reached. In this case $2V4 = V3 + V5$ or the voltage $V5 - V4 = V4 - V3$. When the time interval $t_4 - t_3$ is reduced by the time interval $t_5 - t_4$ or $t_7 - t_8$ is reduced by $t_8 - t_6$, a time interval is obtained which comprises a small remaining dead time which substantially does not influence the measurement of the concentration of the gas component. When the reference value V5 is caused to coincide with the reference value V2, V3 is caused to coincide with V1 and a measurement is carried out over a whole period $t_0$ to $t_2$, it is found that also a small remaining dead time is obtained. The sum of $t_4 - t_0$ and $t_2 - t_8$ minus the sum of $t_2 - t_4$ and $t_8 - t_1$ is then taken, which corresponds to $t_9 - t_8$ minus $t_8 - t_4$. In FIG. 2 it can be seen clearly that now an RC time at 20 is cancelled by the RC time at 19.

Figure 3:
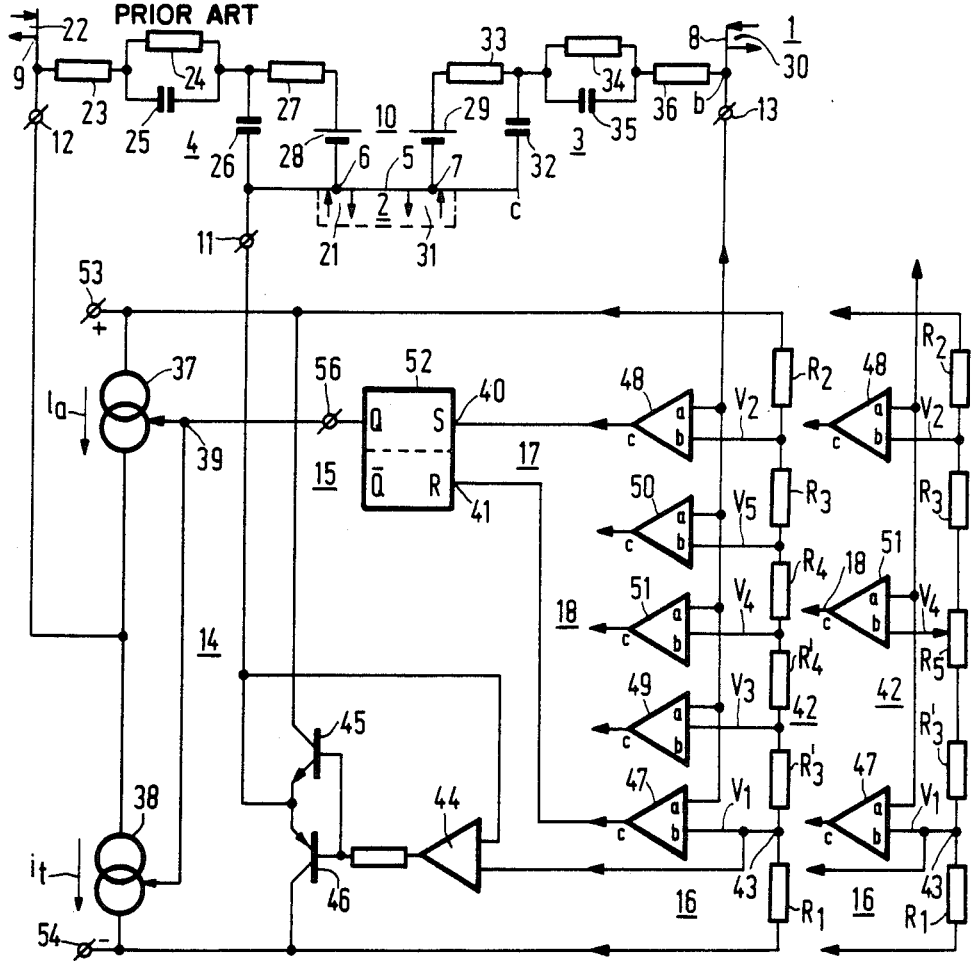
FIG. 3 shows in greater detail a circuit diagram of a gas analysis apparatus according to the invention.

FIG. 3 shows an elaboration of the equivalent circuit diagram of the measuring device and represents an electronic control derived from the known circuit according to the aforementioned United States Patent.

The separation wall portion 4 of the measuring device 10 ensures the gas transport according to arrows 21 from or to the space 2 (shown symbolically) to or from the space 1 or an arbitrary space indicated by the arrows 22. Within the wall portion this transport is realized by means of an ion current, the necessary charge exchange taking place via the electrical current which is supplied to or taken from the terminals 11 and 12. The ion current passes a series resistor 23 and a parallel resistor 24, charge then being required for the capacitance 25, and has to be used to cause the charge of the capacitance 26 to change. The main part of the current flows via a series resistor 27 and a battery 28 representing symbolically the Nernst voltage to or from the electrode layer 6. In the case in which the electrical current between the terminals 11 and 12 is zero, as is indicated in FIG. 1 by the position y of the switch 15, the capacitance 25 is discharged through the resistor 24 and the capacitance 26 is adjusted to the Nernst voltage of the battery 28, which also means fixing of charge. It is clear that the voltage of the battery 28 depends according to Nernst upon the pressure ratio of the gas component at the electrode layer 9 and in the space 2. Similarly, the voltage of the battery 29 represents the Nernst voltage depending upon the pressure ratio in the space 1 and the space 2. The separation wall 3, which can be geometrically equal to the wall 4, is used as a sensor for the Nernst voltage. Since this voltage is measured substantially in an electroless manner, no current flows in the electronic circuit between the terminals 11 and 13. However, in the separation wall 3 an ion current can flow, the ions of which pass into gas molecules in the space 2 at the arrows 30 and in the space 2 at the arrows 31 and at the electrode layers 8 and 7, respectively. The ion current is obtained in that the charge of the capacitance 32 has to be adapted to the varying Nernst voltage caused by the pressure variation in the space 2. This charge adaptation becomes manifest in measuring time, mainly because of the RC time of the resistor 33 and of the capacitance 32 and due to the fact that the gas molecules at the arrows 31 also have to be supplied or removed at the arrows 21. It should be noted that the series resistor 36 is of no importance and the resistor 34 and the capacitance 35 are substantially of no importance for the measurement.

The electronic blocks of FIG. 1 are somewhat further elaborated in FIG. 3, wherein reference can be made to the known literature for the construction of the current sources 37 and 38 with control 39. The switch 15 is constructed also in this case as a flipflop having set and reset inputs 40 and 41 to which the control leads 17 are connected. As is known, the wall portion 5 is held via the terminal 11 at a fixed potential with respect to the electronic circuit with supply by means of a voltage divider 42 with tapping point 43, amplifier 44 and output transistors 45 and 46. The voltage levels $V_1$, $V_2$, $V_3$, $V_4$ and $V_5$ are indicated on the voltage divider 42, $V_1$ obtaining the value zero. The resistors $R_3$ and $R_3'$ and $R_4$ and $R_4'$, respectively, have substantially equal values, while the divider 42 is completed by the resistors $R_1$ and $R_2$. In FIG. 3, A and B indicate that two embodiments of the detection circuit 16 are possible. In the part A, the detection circuit 16 comprises, beside the voltage divider 42, a number of voltage detectors 47–51 for the detection of the levels $V_1$ to $V_5$. An input a of each voltage detector is connected to the terminal 13 and receives the sensor voltage, while the input b is connected to a detection level. The voltage detector 47 detects at its output c that the level $V_1=0$ is reached, as a result of which a "1" signal is supplied to the reset input 41 of the flip-flop 52. The latter produces a "zero" signal at the output "Q" and the current source 37 is switched on for supplying a pumping current, while the filling current $i_f$ is switched off. Successively, the sensor voltage reaches a level $V_3$, which is indicated by voltage detector 49 at its output c, reaches a level $V_4$, which is indicated by the voltage detector 51, reaches a level $V_5$, which is indicated by the voltage detector 50, and reaches a level $V_2$, whereupon the voltage detector 48 supplies a "1" signal at its output c for the set input 40 of the flip-flop 52, as a result of which the output "Q" supplies a "1" signal and the supply current source 38 is switched on, the pumping current $i_a$ being switched off. The various said levels are now passed in the inverse order of succession. At the outputs c of the voltage detectors 49, 50 and 51, the voltage jumps from "0" to "1" and conversely indicate the instants which are denoted in FIG. 2 by $t_3$, $t_4$, $t_5$ and $t_6$, $t_8$ and $t_7$. By means of data processing apparatus with time interval measuring devices which are connected to the outputs 49c, 50c and 51c, the first time interval $t_4-t_3$ or $t_7-t_8$ and the second time interval $t_5-t_4$ or $t_8-t_6$ and also their difference can be determined, which represents the measure of the concentration to be measured.

In FIG. 3, the part B, which can replace the part A, represents a simplified detection circuit 16. The voltage detectors 49 and 50 with their reference levels $V_3$ and $V_5$ are omitted. Their function is taken over by the existing voltage detectors 47 and 48. When, as is shown in FIG. 3, there is switched and measured continuously, the instants $t_3$ and $t_0$, $t_7$ and $t_2$, $t_5$ and $t_1$ and $t_6$ and $t_1$ coincide. In view of the suggested summation of first time intervals and second time intervals, it is sufficient to measure from $t_4$ to $t_8$ and from $t_8$ to $t_9$. These instants are indicated by the output c of the voltage detector 51 in the part B so that this output at the same time constitutes the connection terminal 18 of FIG. 1. In the part B, it is indicated with a potentiometer $R_5$ that the level $V_4$ can still be finely adjusted outside the exact value $2V_4=V_1+V_2$ in order to compensate for non-linearities. These non-linearities are present during the operation of the measuring device 10 and cannot be represented in the equivalent circuit diagram shown in FIG. 3. Such a potentiometer $R_5$ may of course also be included in the divider 42 of the part A, but is not shown for the sake of clarity. The part B is further equal to the part A and can be connected at the area of the arrows. The control 39 of FIG. 3 can further be provided with time delays so that a pumping or filling current is not switched on immediately after a filling or pumping current has been switched off.

The invention was described with reference to an embodiment in which a subatmospheric pressure regularly prevails in the space 2. The invention may also be used in the case where an excess pressure regularly prevails in the space 2 with respect to the space 1. The function of the filling and pumping currents is then interchanged. The Nernst voltage is negative (cf. FIG. 2). The much less steep part of the natural logarithm curve is used so that at the same levels as in FIG. 2, which are now negative, however, much longer times $t_0$ to $t_9$ are obtained (compare the curve 55 in FIG. 2). In FIG. 3, a few connections should be changed when the supply terminal 53 remains positive and the supply terminal 54 remains negative. The connection 56 has to be displaced to the output $\overline{Q}$; the inputs a and b of the voltage detectors have to be interchanged and the voltage divider 42 has to be connected inversely to the supply.

A gas analysis apparatus for oxygen is described by way of example. The measuring device 10 has separation walls 3 and 4 of zirconium dioxide contaminated with, for example, yttrium oxide or calcium oxide, platinum electrode layers 6, 7, 8 and 9 and a platinum ring 5. The space 2 is circular and has a diameter of 1.2 mm and a height of 40 micrometers. The volume is $4.3\times10^{-11}$ m$^3$. The filling and the pumping current are equal to 10 μA. $V_1=0$, $V_2=80$, $V_3=4$, $V_4=40$ and $V_5=76$ mV. The temperature of the measuring device 10 is 700° C. A suitable pressure range to be measured is from 20 mbar ($2\times10^3$ Pa) to 208 mbar ($2.08\times10^4$ Pa). The last-mentioned pressure is the reference pressure of oxygen in the atmospheric air. With the known periodical time measurement there is found: $t=1.3+40.p$. where $t$=measuring time in seconds, 1.3=dead time in seconds, and p=oxygen pressure in bar. The dead time can be eliminated with two calibration points. However, in due course this time changes into a value of, for example, 0.8 seconds. This corresponds to a displacement of 12 mbar, which in a measuring range of from 20 to 200 mbar is too large to measure therein with a certain accuracy.

If now with the same measuring device the measuring method according to the invention is used, in which $V_4$ is chosen to be 34 mV instead of 40 mV, first $t=0.06+26.p$, whereupon in due course $t=-0.05+26.p$, which means a variation corresponding to $+2$ mbar through zero to $-2$ mbar, which variation is acceptable for the measuring range.

What is claimed is:

1. A gas analysis apparatus for measuring the concentration of a gas component in a first space comprising: a sealed measurement space, of which at least one wall portion includes a separation wall which exhibits ionic conduction and is in contact at least in part via an outer side with the first space, a control unit which supplies periodically during a pumping time interval a pumping current to the separation wall so that by means of an ion current in the separation wall the gas component is removed from the measurement space, and which supplies during a filling time interval a filling current whose polarity is opposite to that of the pumping current so that the gas component is supplied to the measurement space, a detection circuit connected to electrode layers on either side of the separation wall, the outer electrode layer of which is in contact with the first space, said detection circuit comprising a first voltage detector which supplies a filling interrupt signal for interrupting the filling current when the electrode voltage across the said electrode layers reaches a first reference value, and a second voltage detector which supplies a pumping interrupt signal for interrupting the pumping current when the electrode voltage reaches a second reference value, the electrical charge provided in the separation wall being measured as a measure of the concentration of the gas component, characterized in that the detection circuit further comprises a third, a fourth and a fifth voltage detector, which supply output signals when the electrode voltage reaches a third, a fourth and a fifth reference value, respectively, all said values lying in the range from the first to the second reference value and twice the fourth value being substantially equal to the sum of the third and the fifth values, while as a measure of the concentration of the gas component a difference charge is measured which is equal to the difference between the charge displaced in a first time interval limited by the instants at which the third and the fourth voltage detectors supply their output signals and the charge displaced in a second time interval limited by the instants at which the fourth and the fifth voltage detectors supply their output signals.

2. A gas analysis apparatus as claimed in claim 1, characterized in that the measurement of the difference charge takes place during the pumping time interval and during the filling time interval.

3. A gas analysis apparatus as claimed in claim 2, characterized in that the filling and the pumping current are equal to the same constant value and the measure of the concentration is the time interval which is obtained by reducing the sum of the first time interval obtained during the supply of the gas component and the first time interval obtained during the removal of the gas component by the sum of the second time intervals obtained in the same manner.

4. A gas analysis apparatus as claimed in claim 1, characterized in that the filling and the pumping current are equal to the same constant value and the measure of the concentration is the time interval which is obtained by reducing the sum of the first time interval obtained during the supply of the gas component and the first time interval obtained during the removal of the gas component by the sum of the second time intervals obtained in the same manner.

5. A gas analysis apparatus as claimed in claim 4, characterized in that the first and third voltage detectors are combined into a first voltage detector and the second and fifth voltage detectors are combined into a second voltage detector and wherein the filling interrupt signal switches on the pumping current and the pumping interrupt signal switches on the filling current, the measure of the concentration being the difference between the time intervals limited by the instants marked by the output signal of the fourth voltage detector.

* * * * *